United States Patent [19]

Hostetler

[11] Patent Number: 5,208,453
[45] Date of Patent: May 4, 1993

[54] DEVICE TO MEASURE THE RATE OF BREAKDOWN-MEDIATED CHARGE TRANSFER ON A DIELECTRIC

[76] Inventor: William B. Hostetler, Skillman, N.J. 08558

[21] Appl. No.: 761,668

[22] Filed: Sep. 18, 1991

[51] Int. Cl.⁵ .............................................. H01J 40/14
[52] U.S. Cl. ......................... 250/214 LA; 250/227.11; 354/3
[58] Field of Search ....... 250/213 VT, 213 R, 227.11, 250/385.2, 326; 354/62, 3

[56] References Cited

U.S. PATENT DOCUMENTS 4,386,834  6/1983  Toolan ..................................... 354/3
4,542,969  9/1985  Omura .................................... 354/3
4,679,924  7/1987  Wamsley ................................. 354/3

Primary Examiner—David C. Nelms
Assistant Examiner—Que T. Le
Attorney, Agent, or Firm—Franklyn Schoenberg

[57] ABSTRACT

Breakdown-mediated charge transfer is made to occur at the surface of a dielectric and its rate is limited by a defined dielectric polarization level and frequency for safe use in a clinical setting. Measurement is accomplished directly by an optical method and indirectly by a high frequency current detection method. The optical method is made reliable through a sealed construction technique. The quality of diagnostic readings supplied by both methods are made more reliable by a repeatable means of force application.

11 Claims, 1 Drawing Sheet

DEVICE TO MEASURE THE RATE OF BREAKDOWN-MEDIATED CHARGE TRANSFER ON A DIELECTRIC

FIELD OF THE INVENTION

This device pertains to the measurement of electrical effects in living tissue near high voltage discharges. It specifically measures the rate and duration of charge-limited breakdown in gas near the contact boundary of an electrically stressed skin-dielectric interface.

BACKGROUND OF THE INVENTION

"Kirlian photography" or the photographic recording of "coronal" images is an area of questionable research carried on for more than 50 years mostly by persons with little education or training in the disciplines of engineering and physical science.

Recently, data collected in India with a Kirlian apparatus, by Ramesh Chouhan has suggested a relationship between percent transmission figures as measured by densitometer readings and the presence and progress of a variety of carcinomas. His unique discovery, is that this correlation appears when the percent transmission variable is measured as a function of time after the skin surface is washed. Thus a new dimension has been added to a procedure previously of doubtful value.

The equipment used to collect this data, however, was unwieldy and not suited to research into the physical processes behind the time variance. There is also a need to make the recording method more accurate and repeatable; a need to make the equipment less expensive and more transportable to make it more reliable and safer to operate; and, further, to make an instrument that will operate in the normal ambient illumination conditions of a clinical setting.

Traditionally, special meanings have been ascribed, and marginal scientific theories put forth, to explain the shapes and even the colors that are present in Kirlian images. And, it has been claimed that these images are a visible manifestation of "auras" that are visible only to certain specially-gifted people. This invention begins working from the assumption that, (given present science and technology), no useful information will be found in the spatial gradations of density in Kirlian film images. It is also assumed, that information extracted from the images recorded by Ramesh Chouhan, using the SINGLE POINT percent transmission method, can be collected equally well by measurement of total illumination from the discharge surrounding a defined AREA of skin. Further, it is also assumed, for a given patient at least, that total charge transferred in breakdown-mediated events is proportional to the integrated value of the associated illumination.

The scientifically accurate view is taken that the illumination producing discharge process occurs as follows: 1) a dielectric plate is polarized by an adjacent polarizing conductor at high electrical potential, 2) the resultant induced surface charge on the far side of the plate will in turn create a potential in that vicinity which is higher than it would otherwise be in a free space condition (no dielectric), 3) skin or some other conductor, where it contacts the dielectric, will supply mobile charge (because it's a conductor), to neutralize the induced surface charge, 4) where the dielectric is NOT contacted, a high potential difference will exist between the skin and the surface of the dielectric, 5) as the potential of the polarizing plate increases, the potential difference between dielectric and skin will increase to the point where electrical breakdown of the intervening gas will occur and charge will be transferred between the skin and dielectric surface, 6) but, because the surface of the dielectric is not a conductor, this breakdown process does not occur all at once, but small area by small area of dielectric is neutralized via breakdown. When the polarizer plate's polarity is reversed, a similar process occurs, but the charge transfer direction is reversed. Polarizer voltage rises to just beyond the breakdown level, so it must be emphasized that the continued breakdown process is dependent upon alternation of the high voltage polarity; multiple high voltage pulses of the same polarity will have little effect after the first breakdown mediated transfer. Once charge has moved, there won't be quite enough potential difference between the skin and any location on the dielectric to start a breakdown in the reverse direction when polarizer voltage drops to zero. This sequence of limited tiny charge transfers, which is qualitatively different than an arc discharge in lightening, for example, makes the process safe from a medical standpoint.

This patent describes the construction of devices that apply basic science and that exploit the stated assumptions. The devices described are new and significant departures from the existing state of the art, such as it is.

SUMMARY OF THE INVENTION

The principle objects of the present invention are to measure as cheaply as possible, the electrical behavior of conductive tissue used as an electrode in a charge-limited electrical breakdown process, and to make the process as repeatable as possible. A thumb will be used for purposes of illustration as an example of skin.

There are provided, two methods of measuring charge transfer rate.

One collects illumination from the entire area of discharge around a thumb and directs it to an inexpensive large area photocell or solar cell. Imaging or non-imaging optics may be used to collect the light. Whatever method is used, there must be no significant change in total illumination delivered to the photocell for small changes in thumb position.

The other method detects the high frequency variations in current that arise when thousands of small surface charge regions are individually neutralized at a high rate. This high frequency current flows in the lead connecting the polarizer supply and the polarizer plate. A properly designed transformer can not only isolate the high voltages on this lead from the low level detection circuitry; it can also block low frequency signals associated with the displacement current that flows through the area of thumb which contacts the dielectric. And, it can transform the high frequency source impedance to better match the high frequency signal detector. And, there are provided, methods to increase reliability and repeatability.

Reliability is greatly increased by the use of a non-imaging light pipe to conduct illumination from the dielectric plate to the photocell. Intimate contact at all points along the optical path exclude dust and the chemically reactive ozone which tend to occlude optical surfaces.

Repeatability is improved by locating the thumb on a reference platform and mounting the entire dielectric plate assembly on a linear movable track with a constant force mechanism. This sets the contact force between thumb and dielectric to a repeatable value. Repeatability is also improved by a baseline technique that subtracts background illumination from measured illumination. The high frequency current measuring method described, eliminates the effect of normal ambient illumination altogether.

Lastly, a method is provided to simulate the old Kirlian technique of single point percent transmission measurements on film, for research purposes.

BRIEF DESCRIPTION OF THE DRAWINGS

For the purpose of illustrating the invention, there are shown in the accompanying drawings forms which are presently preferred; it being understood that the invention is not intended to be limited to the precise arrangements and instrumentalities shown.

DETAILED DESCRIPTION OF THE PREFERRED EMBODIMENTS

Figure 1:
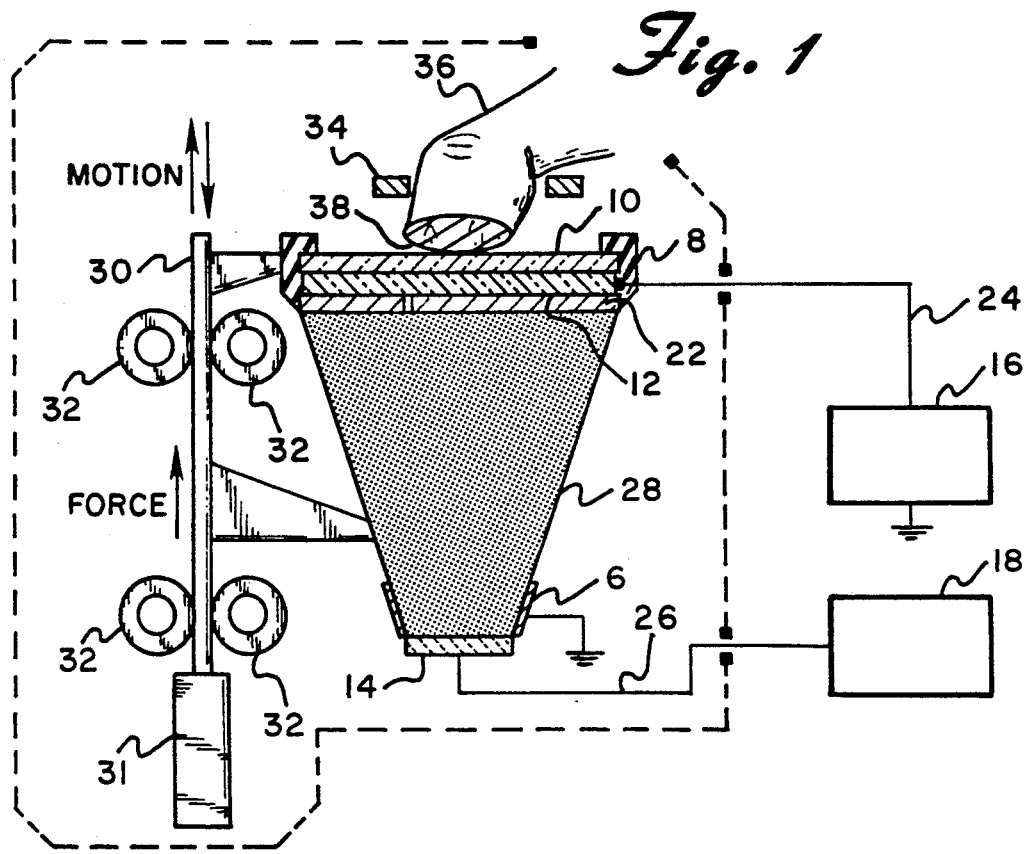
FIG. 1 shows the relationship between the essential components of a device that uses the illumination measurement method. It shows a sectional view of the elements in the optical path which are solids of revolution. Exceptions are, a human thumb 36, and an optional pinhole mask 22. Other components are indicated schematically.

Refer first, to FIG. 1, in the following description of construction details for a device based upon the optical method.

The disc-shaped indium tin oxide (ITO) coated glass plate 10 conductive transparent coating is surrounded by an insulating ring 8 that prevents unwanted light and current generating corona discharge at the sharp edges of the ITO conductive coating. The upper surface of the glass dielectric plate 10 is coating free, and should be sealed to the insulating ring 8 with a high voltage elastomeric O-ring or some adhesive material such as "acetoxy" type silicone rubber adhesive. Differential expansion and contraction of the insulating ring and glass plate make this necessary unless the ring 8 is glass, which is difficult to fabricate. The lower surface of the glass plate 10 has a conductive transparent ITO coating shown in exaggerated form as element 12 in FIG. 1. Electrical connection to this coating must be extremely intimate and extend completely around the periphery of the lower side of the glass plate 10. If contact with the ITO coating is not intimate enough, small sparks will appear, and slowly vaporize the adjacent coating, and eventually create an ITO-free moat around the entire center area (and an inoperable device). Conductive cement such as "nickel print" can be recommended as a reliable, low-resistance contact material. This connection should be passed to a flexible exterior lead 24, and all exposed conductor surfaces and transitions should be thoroughly protected with a high voltage insulating material. Again, acetoxy silicone rubber is highly recommended where moisture can be expelled. A pinhole-aperture mask 22 may be inserted between the light pipe 28, and ITO coating 12 to simulate percent transmission readings of film, but in conjunction with this, it will be necessary to substitute a photomultiplier tube plus support circuitry for the semiconductor photocell 14. The thickness of the mask 22 is exaggerated. If there is no mask, the edges of the light pipe 28 should be sealed to the adjacent insulating ring 8 to permanently exclude dust and ozone. The semiconductor photocell 14 should be placed directly against the face of the small end of the light pipe 28, and the edges sealed with an O-ring or with a small line of elastomeric adhesive. The guard ring 6 reduces the level of induced surface charge appearing at the small end of the light pipe 28 where it is in contact with the photocell 14. The guard ring 6 should, optimally, be a vacuum deposited aluminum coating that does not interfere with TIR on the surface of the light pipe 28. But, a grounded disk of ITO coated glass will also do a good job of reducing electrostatically induced currents in the face of the semiconductor photocell 14, and is much less expensive in small volume.

The above described optical unit is driven through lead 24 by the alternating high voltage polarizer supply 16. The high voltage drive is most easily generated with a step-up transformer of the TV flyback or automobile ignition variety. The important thing is that the frequency of the alternating voltage be high enough that significant current will flow into the parasitic capacitance of the human body, but low enough so that breakdown has time to occur at a reasonable drive voltage. This places frequency nominally between 20 KHz and 50 KHz, and the peak voltage between 10 KV and 20 KV with a 1/16" glass plate 10. The exact waveform of the alternating high voltage drive is unimportant as long as its frequency components are in the proper range. The ringing behavior of the setup transformer will be fixed by its construction, and provides a convenient method of generating a high voltage that alternates, so that the charge transfer process may be reversed. The voltage level however, may be varied conveniently by generating the low voltage primary winding drive signal in a general purpose microprocessor. Within a range of pulse widths less than half the ringing period, a range of peak high voltages may be chosen. This is because the peak current flowing in the high voltage primary is a linear function of the time that a drive voltage is applied, for resultant output voltages in the design range of the transformer. The general purpose microprocessor can also control the period of time between pulses. In the preferred embodiment, this microprocessor communicates with a terminal or host computer for convenient control by an operator. Methods for doing this are well known to any person skilled in the art of constructing computer interfaces, microprocessor assemblies, and electronics at the time of this filing.

The photocell should be connected to the signal processing electronics 18 via a flexible pair 26, which optionally may be shielded. Every time the polarizer supply 16 generates a series of alternating pulses, the photocell 14 detects illumination generated by breakdown events near the dielectric surface 38. The processing electronics 18, should contain an integrator to integrate the illuminating signal over time. Each time a series of ringing pulses are generated, an analog-to-digital converter digitizes the photocell integrator output. At this point, the integrator should be reset so that it is ready for the next integration period. Again, as with the polarizer, these processes can be easily controlled using microprocessor technology that is practiced by many who are skilled in the art. The microprocessor should contain instructions that supply an integrated light reading when the high voltage is not applied so that the effect of ambient light leaking into the light-tight case that encloses the above described device may be subtracted from integrator readings taken with the high voltage on. This reduces the error caused by variable ambient light levels.

An extraneous variable in the discharge is the force between the thumb 36 and the dielectric plate 10. This should be held constant. A reference platform 34 should be located above the movable surface of the glass plate 10, so that when the thumb is in place, the optical assembly will be approximately at the center of its travel. The sliding frame 30, which might have a bar, riding in a set of rollers 32, thus creating a linear translation bearing assembly, should be connected to a negator spring assembly 31 or other constant force device of similar function.

Figure 2:
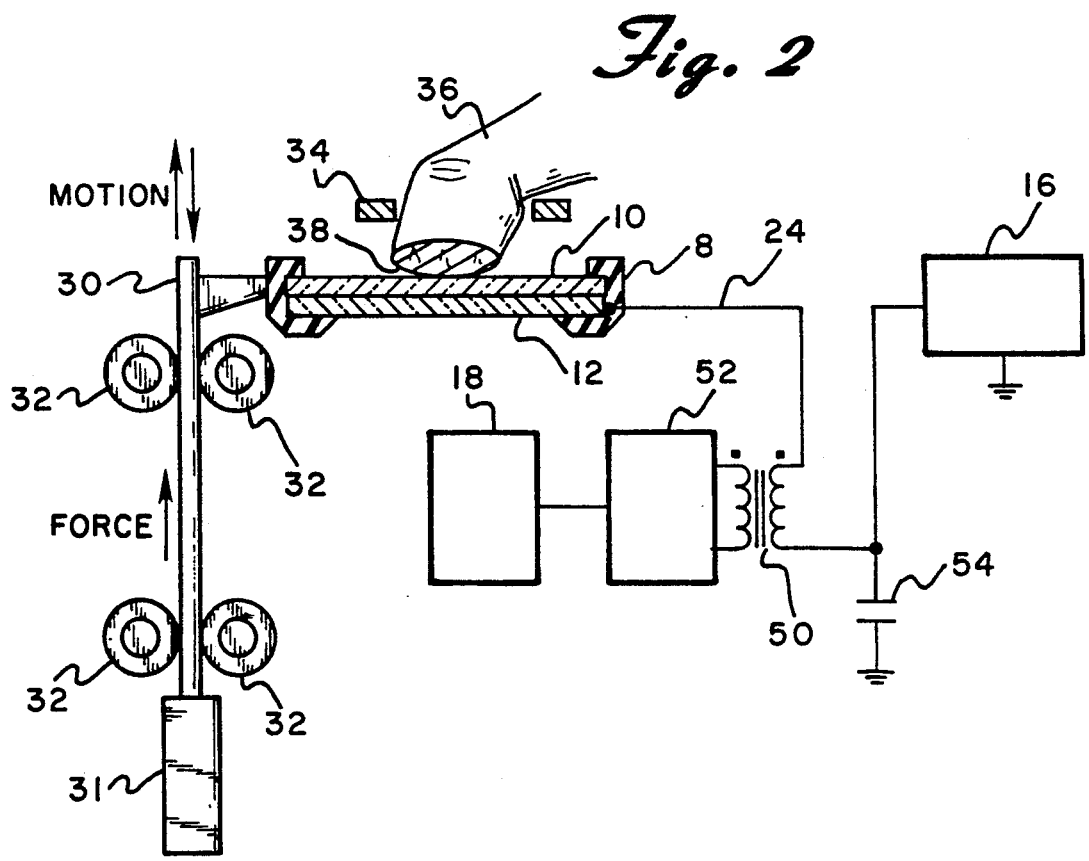
FIG. 2 likewise, illustrates inter-relationships between the essential components of a device that employs the high frequency current detection method.

Refer to, FIG. 2, in the description that follows of the construction of a device based upon the high frequency current measurement method.

This second device is essentially the same in all respects as the optical device, excepting the method of measuring breakdown-mediated charge transfer, and excepting that the polarizer electrode 12 needn't be ITO. It should, however, at least be in intimate contact with the dielectric plate 10. Some type of dielectric cement ought to be used with a metal plate; or, conductive cement might be used alone.

The flexible lead 24 does not go directly to the polarizer supply 16. Instead, the primary of an isolation transformer 50 is placed in series. This can be accomplished by simply passing the flexible lead 24 through the center of a high frequency ferrite toroid, and providing very ample insulation where the lead 24 passes near the ferrite to suppress local corona discharge. The secondary should consist of several turns of litz wire, the number of turns chosen to match the input voltage needs of the high frequency rectifier 52 circuit. The signal so generated will contain frequency components in the nominal radio frequency range, 1 MHz to 10 MHz. The rectifier 52 should produce a signal of amplitude similar to the photocell 14 described in the previous method. A higher signal to noise ratio will be obtained if parasitic inductance can be kept to a minimum. A further increase will be noted if a small, low-inductance, capacitive bypass 54 to ground is added to the polarizer supply 16 output. This is especially true if the polarizer design relies upon a step-up transformer. In this case though, the capacitor should not be so large as to lower the ringing frequency of the transformer below about 20 KHz.

From this point on, the function of the integrating and processing electronics 18, are essentially identical to those described for the optical device. The one exception is that there is now little need for a reference measurement, since normal ambient light will have little effect. Caution should be taken though, to exclude UV. UV will abnormally lower all observed breakdown thresholds where it is able to penetrate.

The high voltage polarizer supply ground should be taken to building ground.

What is claimed is:

1. An optical assembly for collecting and collimating light emitted from a planar corona discharge, comprising in combination, a dielectric plate, a transparent electrode means in intimate contact with a surface of said dielectric plate; a photocell means; and elongated light pipe means intermediate said transparent electrode means and said photocell means having one end thereof in intimate contact with said electrode means and an opposite end in intimate contact with a surface of said photocell.

2. The optical assembly for collecting and collimating light emitted from a planar corona discharge as claimed in claim 1, wherein said optical assembly is a one-piece, sealed, construction that is immune to dust and ozone.

3. The optical assembly according to claim 1, wherein said transparent electrode means comprises a delicate conductive, transparent coating and connection to the delicate conductive, transparent coating is by means of annular application of conductive cement.

4. The optical assembly according to claim 1, wherein electrostatic guarding of the photocell surface is achieved by a vacuum-deposited aluminum ring about said photocell means and light pipe means that preserves internal light reflection therein and is connected to a polarizer supply ground.

5. The optical assembly according to claim 1, wherein a pinhole aperture mask is included between said polarizer electrode and light pipe means that is adapted to simulate traditional measurements of film image densities by a photomultiplier.

6. The optical assembly for collecting and collimating light emitted from a planar corona discharge as claimed in claim 1, wherein force means is applied to said optical assembly that is independent of assembly position.

7. A device for collecting and collimating light emitted from a planar corona discharge, comprising an optical assembly as claimed in claim 1, a bearing mechanism means in association with said optical assembly, and a displacement-independent force means.

8. The optical assembly as claimed in claim 1, wherein said light pipe means is of a frusto conical shape having one large end in contact with electrode means and an opposite smaller end in contact with said photocell means.

9. A non-optical measurement assembly for measuring the level of corona breakdown, comprising a dielectric plate; polarizer electrode means in intimate contact with a surface of said dielectric plate; and electronic analyzing means that utilizes the proportionality between an integrated light value, total breakdown-mediated charge transferred, and an integrated level of rectified high frequency current in a lead connecting a polarizer supply and the polarizer electrode means.

10. A method for measurement of corona discharge intensity, comprising: a) providing a non-optical measurement assembly as claimed in claim 9; b) deposing a test sample in intimate contact with said dielectric plate; c) imposing a force to maintain contact of said test sample and said dielectric plate; and supplying high frequency current to said non-optical measurement assembly.

11. The non-optical measurement assembly for measurement of the level of corona breakdown as claimed in claim 9 wherein said assembly includes, a bearing mechanism means in association therewith, and a displacement-independent force means.

* * * * *